(12) United States Patent
Hartman

(10) Patent No.: US 11,033,492 B2
(45) Date of Patent: Jun. 15, 2021

(54) EQUINE DIETARY SUPPLEMENT

(71) Applicant: Mary Hartman, Rochester, MN (US)

(72) Inventor: Mary Hartman, Rochester, MN (US)

(*) Notice: Subject to any disclaimer, the term of this patent is extended or adjusted under 35 U.S.C. 154(b) by 0 days.

(21) Appl. No.: 16/411,257

(22) Filed: May 14, 2019

(65) Prior Publication Data

US 2020/0360272 A1 Nov. 19, 2020

(51) Int. Cl.

| | |
|---|---|
| A61K 9/00 | (2006.01) |
| A23K 40/20 | (2016.01) |
| A61K 31/7004 | (2006.01) |
| A61K 35/64 | (2015.01) |
| A61K 35/748 | (2015.01) |
| A61K 35/644 | (2015.01) |
| A61K 36/899 | (2006.01) |
| A61K 36/73 | (2006.01) |
| A61K 36/53 | (2006.01) |
| A61K 36/33 | (2006.01) |
| A61K 36/889 | (2006.01) |
| A61K 36/45 | (2006.01) |
| A61K 36/61 | (2006.01) |
| A61K 36/185 | (2006.01) |
| A61K 36/79 | (2006.01) |
| A23K 50/20 | (2016.01) |
| A23K 10/30 | (2016.01) |
| A23K 20/163 | (2016.01) |
| A23K 10/16 | (2016.01) |
| A61K 36/537 | (2006.01) |

(52) U.S. Cl.
CPC ............ *A61K 9/0056* (2013.01); *A23K 10/16* (2016.05); *A23K 10/30* (2016.05); *A23K 20/163* (2016.05); *A23K 40/20* (2016.05); *A23K 50/20* (2016.05); *A61K 31/7004* (2013.01); *A61K 35/64* (2013.01); *A61K 35/644* (2013.01); *A61K 35/748* (2013.01); *A61K 36/185* (2013.01); *A61K 36/33* (2013.01); *A61K 36/45* (2013.01); *A61K 36/53* (2013.01); *A61K 36/537* (2013.01); *A61K 36/61* (2013.01); *A61K 36/73* (2013.01); *A61K 36/79* (2013.01); *A61K 36/889* (2013.01); *A61K 36/899* (2013.01)

(58) Field of Classification Search
None
See application file for complete search history.

(56) References Cited

U.S. PATENT DOCUMENTS

| | | |
|---|---|---|
| 5,792,470 A | 8/1998 | Baumgardner, Sr. |
| 5,853,757 A | 12/1998 | Durand |
| 6,827,965 B1 * | 12/2004 | Fitzpatrick .............. A23P 10/25 426/460 |
| 8,501,218 B2 | 8/2013 | Hurwitz |
| 9,161,960 B2 | 10/2015 | Minatelli |
| 9,498,433 B1 * | 11/2016 | Mullin .................. B65D 65/463 |
| 2004/0185129 A1 | 9/2004 | Vuksan |
| 2008/0194517 A1 * | 8/2008 | Smith ..................... A23K 50/42 514/54 |
| 2011/0118243 A1 * | 5/2011 | Chambers ............ A61K 36/899 514/226.5 |
| 2013/0115266 A1 | 5/2013 | Zulman |
| 2014/0205675 A1 * | 7/2014 | Minatelli ............. A23K 20/158 424/601 |
| 2015/0373950 A1 | 12/2015 | Spring |
| 2018/0317521 A1 * | 11/2018 | Harris .................. A61K 36/258 |

FOREIGN PATENT DOCUMENTS

| | | | | |
|---|---|---|---|---|
| BR | 102013005727 A2 * | 3/2016 | | |
| WO | WO2004022725 | 3/2004 | | |
| WO | WO-2010051814 A1 * | 5/2010 | ............. | A23K 10/18 |

OTHER PUBLICATIONS

Novusera, "10-in-One", novusera.com, published and reviewed in or before 2018 (printed from http://novusera.com/10-in-one-vitamins-superfruits/on Jul. 18, 2020). (Year: 2018).*
"NP Nutra, Nature's Power Nutraceuticals Corp", Food Navigator-USA.com, published on Mar. 15, 2018 (printed from https://www.foodnavigator-usa.com/Suppliers/NP-Nutra-Nature-s-Power-Nutraceuticals-Corp on Jul. 19, 2020). (Year: 2018).*
"Maju Wheatgrass Juice Powder", amazon.com, available on or before Jul. 25, 2017 (printed form https://www.amazon.com/Organic-Wheatgrass-Juice-Powder-Temperatures/dp/B071DDQQY5 on Jul. 19, 2020). (Year: 2017).*
NP Nutra, "Ingredient of the Month: Nopal", npnutra.com, posted on Dec. 5, 2017 (printed from https://npnutra.com/np-nutra-ingredient-of-the-month-nopal.html on Jul. 19, 2020). (Year: 2017).*
Arizona Cactus Ranch, "Prickly Pear Nectar", arizonacactusranch.com, copyrighted 2015 (printed from https://arizonacactusranch.com/product/prickly-pear-nectar-32oz/ on Jul. 18, 2020). (Year: 2015).*
Williams, C., "Specialized dietary supplements", Equine Applied and Clinical Nutrition, 2013, Abstract Topic "Been Pollen", ScienceDirect. (Year: 2013).*
Krahl, S., "Do you feed these 3 beneficial superfoods to your horse?", soulfulequine.com, published at least on or before Nov. 12, 2011 (printed on Jul. 16, 2020 from https://www.soulfulequine.com/nutrition-for-horses-and-spirulina/ (Year: 2011).*
NP Nutra, "NutraGrass", npnutra.com, posted on Oct. 24, 2011 (printed from https://npnutra.com/nutragrass.html on Jul. 19, 2020). (Year: 2011).*
Wolfram, R., et al. "Effect of prickly pear (*Opuntia robusta*) on glucose-metabolism in non-diabetics with hyperlipidemia—study", abstract, Wiener klinische Wochenschrift, Sep. 30, 2002, 114 (19-20), 840-846. (Year: 2002).*
Hamdi, M., "Prickly pear cladodes and fruits as a potential raw material for the bioindustries", Bioprocess Engineering 17 (1997) 387-391. (Year: 1997).*
Ahumada, F. et al., "Studies on the effect of schizandra chinensis extract on horses submitted to exercise and maximum effort", Phytotherapy Research, 1989, vol. 3, No. 5, pp. 175-179. (Year: 1989).*
Author Audi Donamor, Equine Wellness Magazine, Nov. 13, 2017 Title : Chia Cookies for Horses.

* cited by examiner

Primary Examiner — Gina C Justice

(57) ABSTRACT

An equine dietary supplement which is fed to a horse to improve the health of the horse includes a mixture containing chia seeds, whey dextrose and bee pollen.

5 Claims, 1 Drawing Sheet

EQUINE DIETARY SUPPLEMENT

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

(e) INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The invention is in the field feed supplements provided to horses to improve overall health including gastric support, skin and hair conditioning, hoof health, inhibit hives and sweet itch (culicoides hypersensitivity), improve respiratory allergy symptoms and promote healthy hind guy bacteria.

(2) Description of Related Art Including Information Disclosed Under 37 CFR 1.97 and 1.98

The disclosure and prior art relates to animal dietary supplements and more particularly pertains to a new animal dietary supplement which includes ingredient components to enhance the overall health of a horse and to provide pill delivering means.

BRIEF SUMMARY OF THE INVENTION

An embodiment of the disclosure meets the needs presented above by generally comprising a mixture which is fed to horses and includes chia seeds, whey dextrose and bee pollen.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
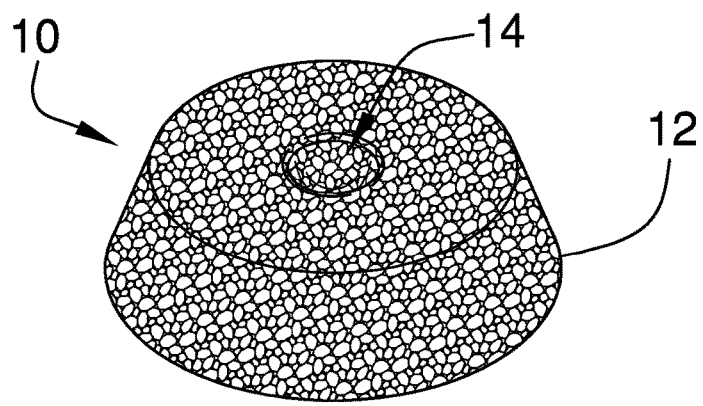
FIG. 1 is a top isometric view of a equine dietary supplement biscuit according to an embodiment of the disclosure.
Figure 2:
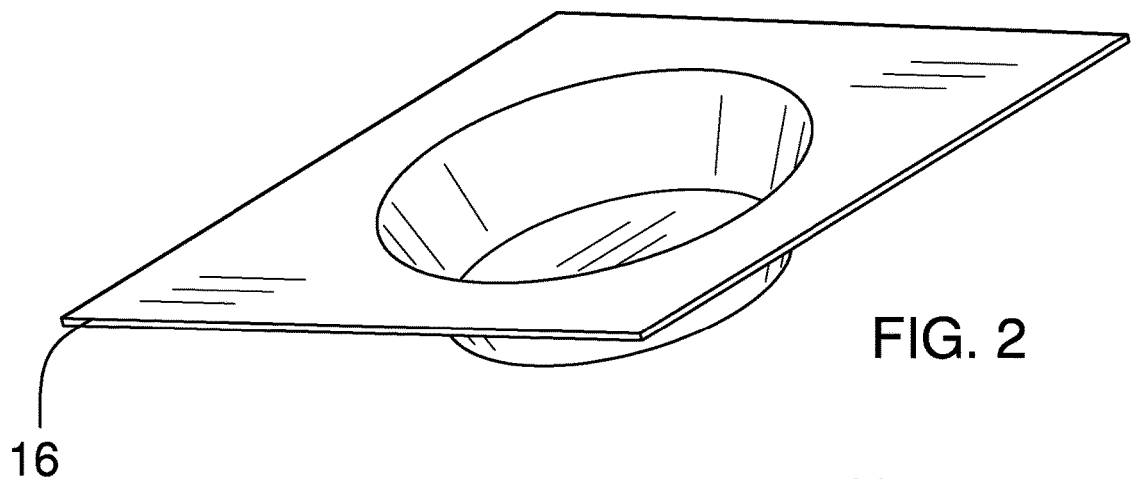
FIG. 2 is a top isometric view of a mold of an embodiment of the disclosure.
Figure 3:
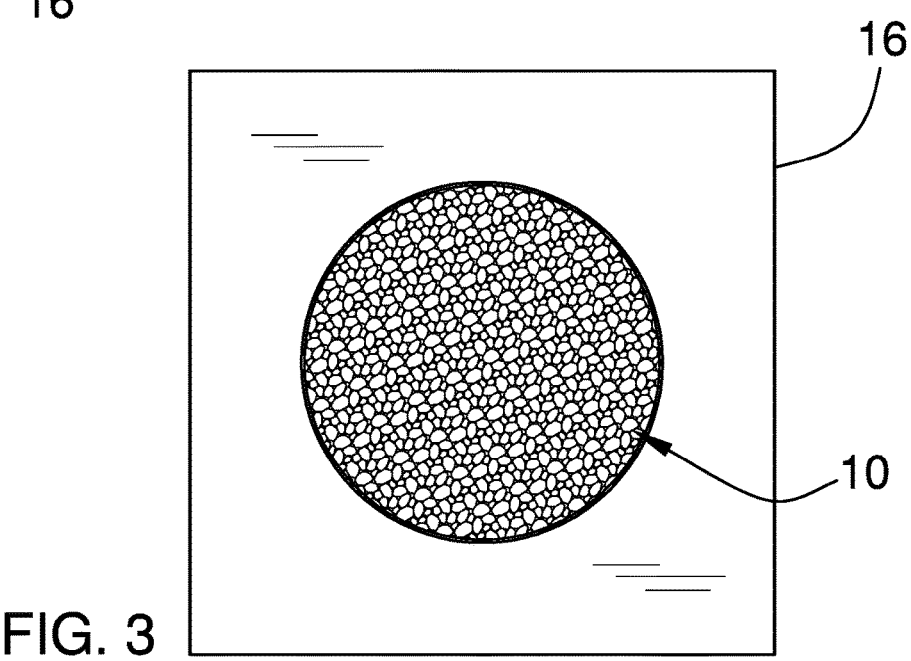
FIG. 3 is a top view of a filled mold of an embodiment of the disclosure.

With reference now to the drawings, and in particular to FIGS. 1 through 3 thereof, a new animal dietary supplement embodying the principles and concepts of an embodiment of the disclosure and generally designated by the reference numeral 10 will be described.

As best illustrated in FIGS. 1 through 3, the equine dietary supplement 10 generally comprises a mixture of a plurality of ingredients that may be fed to a horse in either a biscuit 12 form as shown in FIG. 1 or which may be supplied in a loose, granular form. If a biscuit 12 is utilized, it may include a pill receiving indentation 14 so that the supplement 10 may be utilized for feeding medication or other supplements to the horse.

The equine dietary supplement 10 may be comprised in a plurality of formulations which will typically include some, but not all, of the following ingredients which are listed by their common names and followed by their scientific classification, if needed. Each of the following ingredients is also ubiquitous in the food industry and each is widely available from multiple sources.

Typical Components of the Equine Dietary Supplements:
i. chia seeds, which are typically seeds from *Salvia columbariae* or *Salvia hispanica*
ii. spirulina, a biomass of cyanobacteria including *Anthrospira platensis*
iii. honey, and in particular what is known as Manuka honey containing high concentrations of methylglyoxal, which is measured by a rating called UMF and wherein the honey should have a rating of at least UMF 16, Manuka honey is made from nectar of the Manuka tree, *Leptospermum scoparium*
iv. bee pollen
v. wheatgrass juice powder, wheatgrass is the freshly sprouted first leaves of the common wheat plant, such as *Triticum aestivum*
vi. unsweetened apple puree, the apples used to make the puree may be any common apple sold for human consumption
vii. whey dextrose, which is a combination of whey and dextrose and is provided as a powder
viii. rosemary extract, the extract of rosemary plant needles, *Rosmarinus officinalis*
ix. defatted chia, flour that has had fat removed from the chia seeds x. *Opuntia* cactus powder, commonly known as prickly pear, *Opuntia ficus-indica*
xi. *Opuntia* cactus fruit nectar;
xii. a blend of berries which may be provided in a dried, powdered form, and may include acai (*Euterpe oleracea*), *Aronia* chokeberries (*Aronia arbutifolia, Aronia melanocarpa*, and/or *Aronia prunifolia*), cranberry (*Vaccinium oxycoccos*), jabuticaba (*Plinia cauliflora*), maqui (*Aristotelia chilensis*), pomegranate (*Punica granatum*), and *Schisandra* (*Schisandra chinensis*), one source of such a blend is available under the trade name BettaBerries sold by NP Nutra, 15161 Figueroa Street, Gardena, Calif.
xiii. dried raspberry powder, *Rubus idaeus* and/or *Rubus occidentalis*

In all embodiments, the equine dietary supplement will include a base component mixture containing chia seeds, bee pollen and whey dextrose. For the examples listed below, the amount of the base components will typically include a volume of the chia seeds from 3 cups to 4 cups, a volume of the bee pollen from 3 teaspoons to 5 teaspoons and a volume of the whey dextrose being from 1 teaspoon to 2 teaspoons. The remaining ingredients will be in a ratio to these base components as listed below with tolerance variations of up +/−20% for each ingredient.

The supplement may be provided, as noted below, as a loose material or may be compacted into a biscuit configuration. When provided in the loose condition, it may be added to the feed of a horse.

Specific examples of the equine dietary supplements will now be listed below as well as the method for making each.

Supplement Example #1

3.5 cups of chia seeds;
¼ cup of spirulina;
¼ cup of honey;
¼ cup of bee pollen;
2 tablespoons of wheatgrass juice powder;
1 cup of unsweetened apple puree;
1.5 teaspoons of whey dextrose; and
¼ teaspoon of said rosemary extract.

The chia seeds and whey dextrose are combined until the chia seeds are coated with the whey dextrose. The spirulina and wheat grass juice powder are then added and mixed thoroughly. Into this combination is added the honey, rosemary extract, and the apple puree. Liquid, such as water, may be added to this mixture until the mixture appears to be homogenous. The bee pollen is finally added and the mixture is worked quickly to prevent the chia seeds from opening. The mixture is then scooped and placed into a mold 16. The mold 16 has a rounded perimeter wall and concave depression therein to form a biscuit 12 with the mold 16. The mold 16 should have a size such that approximately 1.2 tablespoons of the mixture fills the mold 16. The mixture is then packed firmly and the mold 16 flipped over. An indentation 14 for receiving a pill is then pushed into the top side of the biscuit 12. The biscuit 12 is placed on a tray and dehydrated for 10 hours at 105 degrees.

Supplement Example #2 (Loose Granular Condition)

3.5 cups of chia seeds;
¼ cup of spirulina;
¼ cup of honey;
¼ cup of bee pollen;
2 tablespoons of wheatgrass juice powder;
1.5 teaspoons of whey dextrose; and
1 tablespoon of water.

The chia seeds and whey dextrose are combined until the chia seeds are evenly coated. The spirulina and wheat grass juice powder are then added. The honey and water (which should be warm enough to combine with the honey) are mixed and then poured in the chia seed mixture. This combination is then mixed until there is a lack of clumping and the chia seeds are adhered to the other dry components. The mixture is placed on a large baking sheet and spread into a thin layer. The mixture is dehydrated for two hours with air circulating over the mixture, such as by a fan on low, at 105 degrees. The bee pollen is then added to the mixture and mixture mixed to evenly distribute the bee pollen. This example does not utilize the mold and is fed to a horse in a loose manner.

Supplement Example #3

3.5 cups of chia seeds;
¼ cup of defatted chia;
¼ cup of dried *Opuntia* cactus powder;
1 cup of *Opuntia* cactus fruit nectar;
¼ cup of blend of berries;
1 teaspoon of dried raspberry powder;
¼ cup of bee pollen;
1.5 teaspoons of whey dextrose; and
¼ teaspoon of said rosemary extract.

The chia seeds and whey dextrose are combined until the chia seeds are evenly coated. The bee pollen, berry mixture, dried raspberry powder and nopal powder are mixed and then added to the chia seed mixture. The rosemary extract and *Opuntia* fruit puree are combined and added to the chia mixture. The entire mixture is then mixed until evenly distributed. The mixture is then scooped and placed into the mold 16 to form the biscuit 12 with the mold 16. The biscuit 12 includes 1.2 tablespoons of the mixture. As previously stated above, the mixture is then packed firmly and the mold 16 flipped over so that an indentation 14 for receiving a pill may be formed into the top of the biscuit 12. The biscuit 12 is placed on a tray and dehydrated for between 6 and 7 hours at 105 degrees.

Supplement Example #4 (Loose Granular Condition)

3.5 cups of chia seeds;
1 tablespoon plus ⅓ cup of dried *Opuntia* cactus powder;
¼ cup of blend of berries;
1 teaspoon of dried raspberry powder;
2 tablespoons of *Opuntia* cactus fruit puree;
¼ cup of bee pollen; and
1 teaspoon of said whey dextrose.

The chia seeds and whey dextrose are combined until evenly distributed onto chia. The powdered nopal, blend of berries and raspberry powder are mixed and then added to the chia seed mixture. Onto this mixture is poured the *Opuntia* cactus fruit puree and the entire mixture combined until no clumps remain and the chia is adhered to the other dry food components. The mixture is placed on a baking sheet, spread thin, and dehydrated at 105 degrees for between 1 and 2 hours with gentle air circulation. The bee pollen is then added to the mixture and the mixture mixed to evenly distribute the bee pollen.

In use, the biscuit 12 is fed, as a supplement, to the horse on at regular intervals of time as needed. Since the supplement helps to regulate the overall health of the horse, the intervals may vary depending on the particular condition of the horse.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An equine dietary supplement comprising:
   a mixture including
      3.5 cups of said Chia seeds,
      1.5 teaspoons of said whey dextrose,
      ¼ cup of said bee pollen,
      ¼ cup of *opuntia* cactus powder,
      1 cup of said *opuntia* cactus fruit nectar,
      1 teaspoon of dried raspberry powder, and
      ¼ cup of a blend of berries including acai, *aronia*, cranberry, jabuticaba, maqui, pomegranate, and *schisandra*;
   said mixture being formed into a biscuit; and
   a pill indent extending into a top of said biscuit.

2. An equine dietary supplement comprising:
   a mixture including
      3.5 cups of said chia seeds,
      ¼ cup of said spirulina,
      ¼ cup of said honey,
      ¼ cup of said bee pollen,
      2 tablespoons of said wheatgrass juice powder,
      1 cup of said unsweetened apple puree,
      1.5 teaspoons of said whey dextrose, and
      ¼ teaspoon of said rosemary extract;
   said mixture being formed into a biscuit; and
   a pill indent extending into a top of said biscuit.

3. An equine dietary supplement comprising:
      3.5 cups of said chia seeds,
      ¼ cup of said spirulina,
      ¼ cup of said honey,
      ¼ cup of said bee pollen,
      2 tablespoons of said wheatgrass juice powder,
      1.5 teaspoons of said whey dextrose, and
      1 tablespoon of water;
   said mixture being formed into a biscuit; and
   a pill indent extending into a top of said biscuit.

4. The equine dietary supplement according to claim 1, wherein said mixture further includes:
   ¼ cup of defatted chia;
   and
   ¼ teaspoon of said rosemary extract.

5. The equine dietary supplement according to claim 1, wherein said mixture comprises:
   an additional 0.1425 cups of said dried *opuntia* cactus powder;
   2 tablespoons of *opuntia* cactus fruit puree;
   and
   an additional 0.5 teaspoon of said whey dextrose.

* * * * *